United States Patent [19]

Peter

[11] Patent Number: 5,332,821

[45] Date of Patent: Jul. 26, 1994

[54] PROCESS FOR PREPARING ISOQUINOLINES

[75] Inventor: Philippe Peter, Visp, Switzerland

[73] Assignee: Hoffmann-La Roche Inc., Nutley, N.J.

[21] Appl. No.: 821,105

[22] Filed: Jan. 15, 1992

Related U.S. Application Data

[63] Continuation of Ser. No. 504,823, Apr. 5, 1990, abandoned, which is a continuation of Ser. No. 167,076, Mar. 11, 1988, abandoned.

[30] Foreign Application Priority Data

Mar. 20, 1987 [CH] Switzerland .................. 1064/87

[51] Int. Cl.$^5$ .......................................... C07D 217/20
[52] U.S. Cl. ................................................ 546/144
[58] Field of Search ....................................... 546/144

[56] References Cited

U.S. PATENT DOCUMENTS 3,479,358 11/1969 Hausen et al. ............... 546/144
4,707,485 11/1987 Kaiser et al. ................ 546/144

FOREIGN PATENT DOCUMENTS

| | | |
|---|---|---|
| 834103 | 3/1952 | Fed. Rep. of Germany . |
| 908138 | 4/1954 | Fed. Rep. of Germany . |
| 937589 | 1/1956 | Fed. Rep. of Germany . |
| 955769 | 1/1957 | Fed. Rep. of Germany . |
| 1003211 | 2/1957 | Fed. Rep. of Germany . |

OTHER PUBLICATIONS

Barton, International Series of Monographs In Organic Chemistry, vol. 8, Part IIA Morphinans, pp. 10-32 (1966).
Sugimoto, et al., Studies on the Synthesis of Hydrogenated Quinolines and Isoquinolines as Anagesics, Chem. Pharm. Bull 6, 429 (1958).
Meyers, et al. An Asymmetric Synthesis of (+)-Morphinans in High Enantiomeric Purity, J. Org. Chem. 51, 872 (1986).
Reimann, et al., Selective Catalytic Hydrogenations and Hydrogenolyses, Arch. Pharm. 318, 685 (1985).
Grewe, et al., Annalen Der. Chemie, Preparation of Octahydro Isoquinoline Derivatives by Cyclization (1953).

*Primary Examiner*—C. Warren Ivy
*Assistant Examiner*—Zinna N. Davis
*Attorney, Agent, or Firm*—George M. Gould; George W. Johnston; Ellen Ciambrone Coletti

[57] ABSTRACT

A process for the preparation of isoquinolines of the formula

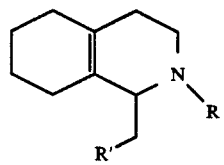

I wherein R is methyl or benzyl and R' is phenyl, p-hydroxyphenyl or p-methoxyphenyl, by reacting a solution of an enamine of the formula

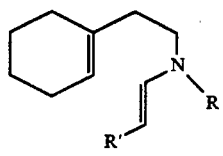

II wherein R and R' are as described above, in a hydrocarbon with an anhydrous solution of p-toluenesulphonic acid in toluene or xylene at an elevated temperature.

10 Claims, No Drawings

PROCESS FOR PREPARING ISOQUINOLINES

This is a continuation, of application Ser. No. 07/504,823 filed apr. 5, 1990, now abandoned which is a continuation of Ser. No. 167,076, filed Mar. 11, 1988, now abandoned.

BRIEF SUMMARY OF THE INVENTION

The invention relates to a process for preparing isoquinolines of the formula

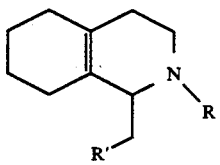

I wherein R is methyl or benzyl and R' is phenyl, p-hydroxyphenyl or p-methoxyphenyl, which process comprises reacting a solution of an enamine of the formula

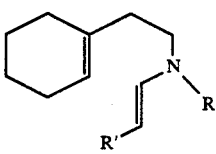

II wherein R and R' are as described above in a hydrocarbon with an anhydrous solution of p-toluenesulphonic acid in toluene or xylene at an elevated temperature.

DETAILED DESCRIPTION OF THE INVENTION

As used herein, hydrocarbon denotes a compound consisting only of carbon and hydrogen.

The invention relates to a process for preparing isoquinolines of the formula

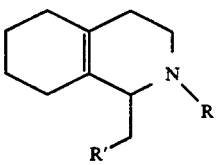

I wherein R is methyl or benzyl and R' is phenyl, p-hydroxyphenyl or p-methoxyphenyl, which process comprises reacting a solution of an enamine of the formula

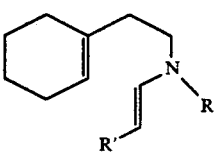

II wherein R and R' are as described above in a hydrocarbon with an anhydrous solution of p-toluenesulphonic acid in toluene or xylene at an elevated temperature.

Aliphatic hydrocarbons such as n-hexane or, preferably, aromatic hydrocarbons such as toluene or xylene are conveniently used as the hydrocarbon. The reaction is conveniently carried out at between about 90° and 115° C., preferably at about 110° C. where R is methyl and at about 100° C. where R is benzyl.

In addition to the isoquinoline of formula I there are also obtained small amounts (4–7%) of the isomeric isoquinolines of the formulae

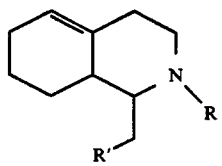

Ia

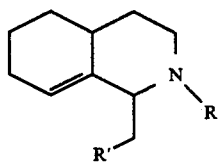

Ib

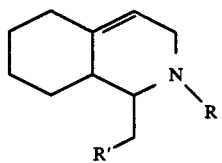

Ic wherein R and R' are as described above. If desired, these by products can be isomerized to the isoquinolines of formula I, which can be carried out under the same process conditions as in the case of the conversion of the enamines of formula II into the isoquinolines of formula I by reaction with p-toluenesulphonic acid.

The starting enamines of formula II can be prepared by a) reacting a solution of an amine of the formula

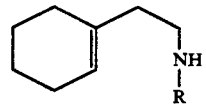

III wherein R is methyl or benzyl, in toluene or xylene while heating with a solution of an aldehyde of the formula R'CH$_2$CHO, wherein R' is phenyl. p-hydroxyphenyl or especially p-methoxyphenyl, in toluene or xylene, or b) reacting a solution of the amine III in a hydrocarbon, especially an aliphatic hydrocarbon such as n-hexane, while heating, optionally under reduced pressure, with an ethereal solution of the aldehyde R'CH$_2$CHO.

As the hydrocarbon in process variant b) there can be used one which is suitable for the conversion of a compound of formula II into a compound of formula I, preferably n-hexane. Water and toluene or xylene are distilled off in process variant a) and water and ether are distilled off in process variant b).

Amines of formula III are known or can be prepared in accordance with known methods. Aldehydes of formula R'CH$_2$CHO, wherein R' is as described above, are known or can be prepared in accordance with known methods.

The solution of the aldehyde R'CH₂CHO in toluene or xylene, which is used in process variant a), can be obtained by heating to reflux temperature a suspension of an alkali metal salt or alkaline earth metal salt of the corresponding glycidic acid of the formula

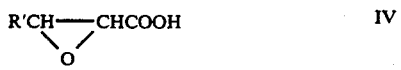

preferably potassium glycidate, in toluene or xylene in the presence of aqueous acetic acid. Glycidic acids of formula IV are known or can be prepared in accordance with known methods. The ethereal aldehyde solution which is used in process variant b) can be obtained by treating a suspension of a sulphonate of the formula

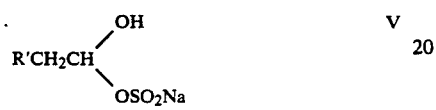

in aqueous diethyl ether in the presence of potassium carbonate at a temperature of about 1°–3° C. The sulphonates of formula V are known or can be prepared in accordance with known methods.

The compounds of formula I can be converted as described e.g. in Swiss Patent Specification No. 543514 into morphinans such as dextromethorphan.

The process of the invention is carried out as shown in the examples below. Temperatures are in degrees celsius unless otherwise indicated.

Example 1 a) 70 ml of an aqueous solution of 3.64 g of acetic acid are added dropwise to a mixture, heated to the boiling point, of 14 g (59 mmol) of potassium (E)-α,β-epoxy-p--methoxycinnamate, 112 ml of toluene and 28 ml of water. After 5 minutes the mixture is cooled to room temperature. The organic phase is washed with water and then with aqueous potassium carbonate solution. The aqueous washings are extracted with toluene. The organic phase is dried azeotropically. The yield of p-methoxyphenylacetaldehyde in the solution obtained amounts to 92–94%.

b) The solution of p-methoxyphenylacetaldehyde in 200 ml of toluene, prepared according to Example 1a), is added under reflux within one hour to a mixture of 78 g (55.5 mmol) of N-methyl-2-(cyclohexen-1-yl)ethylamine in 20 ml of toluene. After 1 hour under reflux there is obtained N-[(E)-p-methoxystyryl]-N-methyl-2-(cyclohexen-1-yl)ethylamine (yield 95.3%) dissolved in toluene.

c) The solution prepared according to Example 1b) is added to a solution of dry p-toluenesulphonic acid (corresponding to 60 g of Bonohydrate) in 600 ml of toluene. After heating under reflux for 3 hours the mixture is cooled and made alkaline with 40% sodium hydroxide solution. After extraction with toluene, washing with water and concentration of the organic phase there is obtained an oil which is distilled at 190° C. under 1 mbar. There are obtained 13.6 g of a clear oil with a content of 1-(p-methoxybenzyl)-2-methyl-1,2,3,4,5,6,7,8-octahydroisoquinoline of 90.8% (yield 83%) and a content of the isomers 1-(p-methoxybenzyl)-2-methyl-1,2,3,4,6,,8,8a-octahydroisoquinoline, 1-(p-methoxybenzyl)-2-methyl-1,2,3,4,4a,5,6,7-octahydroisoquinoline and 1-(p-methoxybenzyl)-2-methyl-1,2,3,5,6,7,8,8a-octahydroisoquinoline of all together 5%.

d) 16.3 g of oxalate are precipitated by means of 4.5 g of oxalic acid in 190 ml of acetone. The mixture of isomeric isoquinolines isolated from the mother liquor is isomerized to a large part to 1-(p-methoxybenzyl)-2-methyl-1,2,3,4,5,6,7,8-octahydroisoquinoline by treatment with p-toluenesulphonic acid as described in Example 1c). 0.66 g of oxalate is obtained from this mixture by again precipitating with 0.56 g of oxalic acid in 15 ml of acetone. After liberation of the oxalate there are obtained 12.7 g (yield 83.5% based on the starting amine) of more than 99% pure 1-(p-methoxybenzyl)-2-methyl-1,2,3,4,5,6,7,8-isoquinoline.

EXAMPLE a) 16.8 ml of an aqueous solution of 10 g of potassium carbonate are added within 5 minutes to a mixture, cooled to 1°–3° C., of 8.2 g (33 mmol) of sodium 1-hydroxy-2-(p--methoxyphenyl)ethylsulphonate, 8.4 ml of water and 84 ml of diethyl ether. The mixture is left to warm to room temperature for 1 hour and 126 ml of water are then added. The organic phase is washed with water and the aqueous phase is washed with ether. The organic phase is then dried over sodium sulphate. The yield of p-methoxyphenylacetaldehyde amounts to 57%.

b) The 125 ml of the ethereal p-methoxyphenylacetaldehyde solution prepared according to Example 2a) are added slowly to a solution of 3.48 g (16 mmol) of N-benzyl-2-(cyclohexen-1-yl)ethylamine in hexane at 50° C. The reaction water and the ether are distilled off. After reaction for 4 hours the resulting solution of N-benzyl-2-(cyclohexen-1-yl)-N-[(E)-p-methoxystyryl]ethylamine is added at 100° C. to a solution of 36 g of p-toluenesulphonic acid in 250 ml of toluene. After reaction for 2 hours the mixture is cooled and made alkaline with sodium hydroxide solution. The organic phase is washed with water. The aqueous phase is extracted with toluene. The organic phase is dried over sodium sulphate, filtered and evaporated. There are obtained 5.72 g of an oil with a content of 2-benzyl-1-(p-methoxybenzyl)-1,2,3,4,5,6,7,8-octahydroisoquinoline of 76.5%. Yield 79% based on the starting amine.

I claim:

1. A process for preparing isoquinolines of the formula

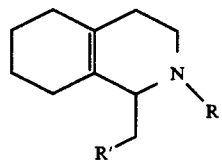

wherein R is methyl or benzyl and R' is phenyl, p-hydroxyphenyl or p-methoxyphenyl, which process comprises reacting a solution of an enamine of the formula

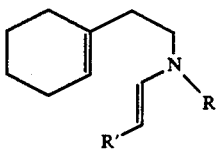

wherein R and R' are as described above, in a hydrocarbon with an anhydrous solution of p-toluenesulphonic acid in toluene or xylene at an elevated temperature.

2. A process according to claim 1, wherein R' is p-methoxyphenyl, an aromatic hydrocarbon selected from the group consisting of toluene and xylene is used as the hydrocarbon and the reaction temperature is between about 90° and about 115° C.

3. A process according to claim 2, wherein R is methyl, and the reaction temperature is about 110° C.

4. A process according to claim 2., wherein R is benzyl, and the reaction temperature is about 100° C.

5. A process for the preparation of an enamine of the formula

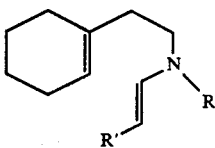

wherein R is methyl or benzyl and R' is phenyl, p-hydroxyphenyl or p-methoxyphenyl which process comprises reacting a solution of an amine of the formula

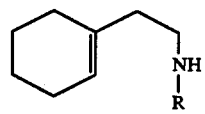

wherein R is methyl or benzyl, in toluene or xylene while heating with a solution of an aldehyde of the formula R'CH$_2$CHO, wherein R' is phenyl, p-hydroxyphenyl or p-methoxyphenyl, in toluene or xylene.

6. A process according to claim 5, wherein R' is p-methoxyphenyl.

7. A process for the preparation of an enamine of the formula

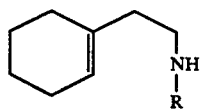

wherein R is methyl or benzyl and R' is phenyl, p-hydroxyphenyl or p-methoxyphenyl which process comprises reacting a solution of an amine of the formula

III

[structure]

in a hydrocarbon, while heating with an ethereal solution of the aldehyde R'CH$_2$CHO.

8. A process according to claim 7, wherein the hydrocarbon is an aliphatic hydrocarbon.

9. A process according to claim 8, wherein the aliphatic hydrocarbon is n-hexane.

10. A process according to claim 7, wherein the heating is conducted under reduced pressure.

* * * * *